US00PP16663P2

(12) United States Plant Patent
Friday

(10) Patent No.: US PP16,663 P2
(45) Date of Patent: Jun. 20, 2006

(54) PEACH TREE NAMED "P.F. 22-007"

(50) Latin Name: *Prunus persica*
Varietal Denomination: P.F. 22-007

(76) Inventor: Paul Jan Friday, P.O. Box 850, Coloma, MI (US) 49038

( * ) Notice: Subject to any disclaimer, the term of this patent is extended or adjusted under 35 U.S.C. 154(b) by 10 days.

(21) Appl. No.: 10/702,923

(22) Filed: Nov. 7, 2003

(51) Int. Cl.
*A01H 5/00* (2006.01)

(52) U.S. Cl. ..... Plt./198
(58) Field of Classification Search ..... Plt./198
See application file for complete search history.

*Primary Examiner*—Kent Bell
*Assistant Examiner*—W C Haas

(57) ABSTRACT

A new and distinct variety of peach, {*Prunus persica*}, tree having the following unique combination of desirable features:

1. Producing a very firm fruit having a resilient flesh texture.
2. Blossoms are non-showy when in full bloom.
3. A substantially spheriodal fruit with yellow flesh having red mottling.
4. Produces fruit of excellent taste.
5. A mid to late season peach variety which matures after Redhaven {non-patented} and which has good storage and shelf life.

1 Drawing Sheet

Botanical classification: *Prunus persica.*
Variety designation: 'P.F. 22-007'.

ORIGIN OF VARIETY

The new peach tree {hereinafter referred to as the 'P.F. 22-007' peach tree} was originated by Paul Friday in an experimental orchard, which is maintained for the purposes of breeding peach trees, located in Coloma, Mich. Coloma is located in the southwest section of Michigan, USDA Zone 6a.

In an ongoing mass selection breeding program, superior seedlings of unrecorded parentage are maintained as seed sources for the production of seeds which are collected and planted in mass. The seed producing parent trees are maintained solely as proprietary trees for breeding purposes and have not been released from the experimental orchard, where such trees can be evaluated for their adaptability to local and regional growing conditions. Seeds resulting from open pollinations of the trees in the experimental orchard are regularly planted in mass to produce new populations of seedlings which are cultured and monitored to maturity. Trees with superior attributes are retained for further observation and testing, and contribute seeds to advancing generations of new populations of seedlings.

The tree of this application, 'P.F. 22-007', was a single plant from one such a seedling population, and was based on the numerous superior genetic attributes of this tree which are described in the botanical description to follow. While not comprehensive, the details of the botanical description to follow are believed to be a reasonably complete botanical description of the tree of this disclosure.

ASEXUAL REPRODUCTION OF THE VARIETY

The new and distinct variety of peach tree was asexually propagated by budding as performed in an experimental orchard, located in Coloma, Mich. The asexual propagation demonstrates that such reproduction of characteristics of the tree are consistent and established and transmitted through succeeding propagation.

SUMMARY OF THE VARIETY

The new and distinct variety of peach tree is of moderate upright growth and a regular and productive bearer of peaches. The blossoms are characterized by being contracted or partially spread when in full bloom.

The blossoms of the present peach tree at full bloom may be characterized as being non-showy, i.e., angularly spaced five blossom petals projecting upwardly at an inclined angle so as to form a blossom, having a diameter of about 1" measured across the blossoms. The typical non-showy bloom as exemplified for example by the Redhaven peach {non patented} has five {5} radically extending and angularly spaced petals projecting upward at a relatively steep inclined angle so that the diametrical measurement across the outer edges of the petals is about 1".

The flesh of the fruit of the present peach tree is firm and is yellow with some red mottling in the flesh.

The skin is smooth and is of dark red color over about eighty (80%) percent of its surface at maturity. The red color occurs over about sixty (60%) percent of the surface about 10 days prior to maturity. At maturity the peach is substantially spheroidal but with a pronounced suture with the diameter ranging between about 2½" to 3" inches.

It is noteworthy that the fruit of this tree is further characterized as having smooth, gently rounded cheeks at the blossom end of the fruit. These protude to form fruit surfaces higher than the blossom point. This characteristic reduces fruit damage in harvest, shipping and storage, by reducing the exposure of and damage to the apical blossom protrusion in handling. Thus breaching of the skin and formation of an entry point for microorganisms which cause rot in many other commercially important peach varieties harvested in the same production period is reduced in this fruit.

The fruit has a firm flesh and may be described as resilient to the extent that the flesh is yieldable and restorable to its original state when subjected to impact forces which may cause permanent deformities in peached of the commercial varieties. The firmness of the fruit facilities handling and packaging of the peaches without damaging the same for shipment. This results in less spoilage and also increases the shelf life.

The fruit matures in the middle to late part of the peach growing seasons of Southwestern Michigan. The fruit as mentioned herefore is of red color over about eighty (80%) percent of its spheroidal surface and has a very attractive appearance.

BRIEF DESCRIPTION OF THE PHOTOGRAPHS

In the accompanying photographic illustrations, the top photograph shows two whole fruit with a third fruit bisected across the axis showing the extent of the red coloration of flesh from the pit well. The otherwise clear yellow flesh is also shown. A tape measure is included to show the good size of this fruit. The bottom photograph depicts the terminal portion of the typical branch of this tree taken at about the time of fruit maturity, showing the size of the leaves, the internode length, and the characteristics of the bark of the current season's growth. A tape measure is included showing the length of a leaf.

DESCRIPTION OF VARIETY

The detailed botanical description of the foliage and fruit of the new variety of peach tree is based upon observations of the specimen grown own its own roots at Coloma, Mich., USDA Zone 6a, with the color terminology, other than the terminology expressed in common terms, in accordance with the Pantone Matching System (PMS) as used internationally to identify printed colors.

Botanical classification: *Prunus persica* cultivar 'P.F. 22-007'.

Tree:
- *Age.*—Ten (10) years.
- *Height.*—Unpruned 8.5'.
- *Width.*—Unpruned 8'.
- *Size.*—Medium.
- *Vigor.*—Medium about two (2) feet growth per year.
- *Density.*—Medium, pruning required.
- *Form.*—Spreading.
- *Production.*—Good, about 1½ bushels per tree per year.
- *Bearer.*—Very productive and cold hardy.
- *Disease resistance to bacterial leaf and fruit spot.*—Very Resistant.

Trunk:
- *Bark color.*—Gray (pantone # 422).
- *Size.*—Medium.
- *Surface.*—Smooth.
- *Diameter.*—2¾" at 18" above ground at 10 years of age.
- *Lenticels.*—Smooth.
- *Lenticels color.*—Light brown (pantone # 471).
- *Lenticels size.*—¼" to ⅜".

Branches:
- *Size.*—Medium to thin — 1⅞" diameter.
- *Surface.*—Smooth.
- *Branch color.*—Gray (pantone # 435).
- *Lenticels per square inch on branch.*—Seven (7).
- *Lenticels size.*—⅛" to 3/16".
- *Lenticels color.*—Tan (pantone # 453).
- *Crotch angles.*—Natural right angles.
- *Internode length.*—⅞".

Leaves:
- *Size.*—Average length 5½" — average width 1⅜".
- *Form.*—Lanceolate — pointed.
- *Thickness.*—Medium.
- *Texture.*—Glabrous.
- *Margin.*—Serrated.
- *Petiole length.*—½".
- *Gland number.*—1 to 2 on each side of the basal portion of the leaf.
- *Gland color.*—Dark Red.
- *Gland shape.*—Oval.
- *Color.*—Upper surface green (pantone # 350) — lower surface green (pantone # 371).

Flower buds:
- *Size.*—½" long — 5/16" wide.
- *Shape.*—Ovoid.
- *Color.*—Pink (pantone # 211).

Flowers:
- *Blooming period.*—Apr. 27, 2003 to May 3, 2003.
- *Bloom size.*—1" diameter.
- *Shape of petals.*—Cupped.
- *Size of petals.*—½" long — ⅜" wide.
- *Number of petals.*—Five (5).
- *Petal color.*—Light pink (pantone # 243).
- *Sepal size.*—5/16" long — 3/16" wide.
- *Sepal shape.*—Cupped.
- *Sepal color.*—Pantone # 391.
- *Number of anthers.*—30.
- *Anthers color.*—Pantone # 168.
- *Number of stamens.*—30.
- *Stamen length.*—5/16".
- *Stamen color.*—Pantone # 417.
- *Pistil length.*—⅜".
- *Pistil color.*—Pantone # 380.
- *Pollen.*—Present.
- *Flowers per cluster.*—Two (2).
- *Flower and petal color.*—Light pink (pantone # 243).
- *Fragrance.*—Mild.

Fruit:
- *Maturity when described.*—Firm ripe.
- *Date of first picking.*—Aug. 23, 2003.
- *Date of last picking.*—Aug. 31, 2003.
- *Size.*—2¾" to 3" diameter.
- *Form.*—Spherical.
- *Suture.*—Some what pronounced and firm.
- *Weight.*—8 oz.

Skin:
- *Thickness.*—Medium.
- *Texture.*—Medium.
- *Tendency to crack.*—None.
- *Down.*—Moderate to little.
- *Color.*—Red {pantone # 187} over yellow {pantone # 110}.

Flesh:
- *Texture.*—Firm, non melting, free of fiber.
- *Ripens.*—Evenly.
- *Flavor.*—Excellent.
- *Aroma.*—Good.
- *Eating quality.*—Excellent, very sweet [sugar content was tested as tested 14 brix].

*Color.*—Light yellow pantone # 128.
*Pit cavity color.*—Red pantone # 179.

Stone:

*Type.*—Freestone.
*Size.*—Noteworthy large size 1 9/16" long — 1 1/4" wide — 11/16" thick.
*Form.*—Ovoid.
*Base.*—Straight.
*Apex.*—Pointed.
*Sides.*—Unequal.
*Surface.*—Furrowed.
*Color.*—Brown [pantone # 181].
*Tendency to crack.*—Very little.
*Kernel.*—White when harvested 13/16" long — 7/16" wide — 1/4" thick.

Use: Dessert.
Shipping quality: Excellent.
Keeping quality: Very Good.

The tree and its fruit herein described may vary in slight detail as a result of differences in climatic or soil conditions or cultural practices under which the tree may be grown. It is to be understood that the description of the new variety as set forth herein is that of the tree grown under the ecological conditions prevailing at Coloma, Mich.

What is claimed is:

1. A new and distinct variety of peach tree as herein illustrated and described.

* * * * *

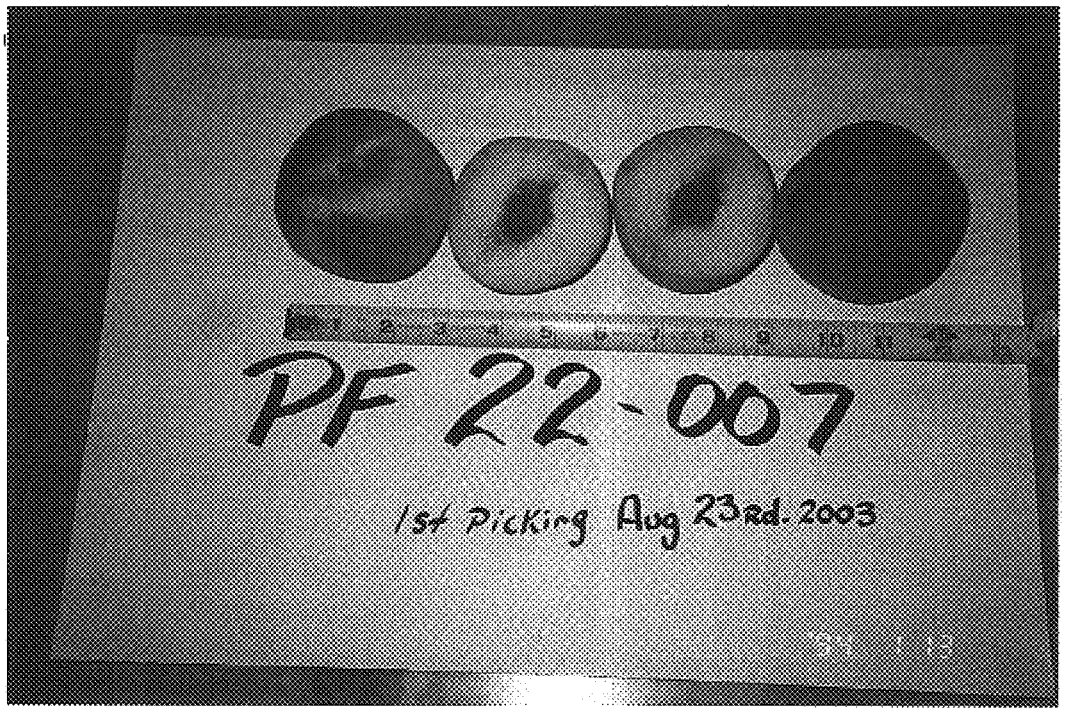
PF 22-007
1st Picking Aug 23rd. 2003
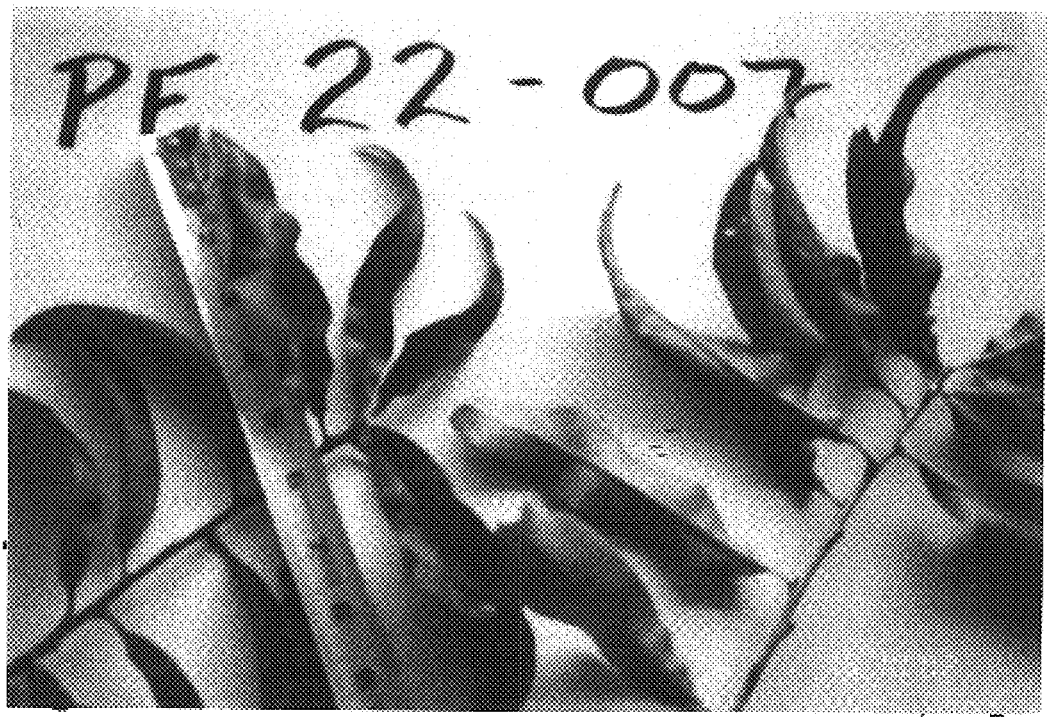
PF 22-007